United States Patent [19]

Gigante

[11] 4,247,287
[45] Jan. 27, 1981

[54] DENTURE AND ARTICLE FOR MAKING SAME

[76] Inventor: John Gigante, 600 Hilltop Ter., Cliffside Park, N.J. 07010

[21] Appl. No.: 15,857

[22] Filed: Feb. 26, 1979

Related U.S. Application Data

[62] Division of Ser. No. 840,154, Oct. 7, 1977, Pat. No. 4,161,065.

[51] Int. Cl.³ .............................................. A61C 13/00
[52] U.S. Cl. ............................. 433/199; 260/31.8 W; 264/18; 433/37; 433/171; 433/172; 433/201
[58] Field of Search ................ 260/31.8 R, 31.8 W; 264/17, 18; 433/37, 171, 172, 199, 201

[56] References Cited

U.S. PATENT DOCUMENTS

| | | | |
|---|---|---|---|
| 2,569,767 | 10/1951 | Knock | 433/199 |
| 2,685,133 | 8/1954 | Greene et al. | 433/171 |
| 2,848,750 | 8/1958 | Sannecke et al. | 264/17 |
| 3,727,309 | 4/1973 | Huey | 433/171 |
| 3,839,796 | 10/1974 | Hazar | 433/171 |
| 3,969,303 | 7/1976 | Prosen | 260/31.8 C |
| 4,184,253 | 1/1980 | Tureaud | 433/171 |

Primary Examiner—Lorenzo B. Hayes
Attorney, Agent, or Firm—Leonard W. Suroff

[57] ABSTRACT

The present invention relates to an article for use in creating a prosthetic denture device that is an impression tray or a denture component formed of a set of hard teeth bonded within a frame assembly formed of a permanent substantially rigid hard frame portion and an adjustable frame portion that is integrally joined to the rigid frame portion and forms part of the frame assembly. The adjustable frame portion is formed from a second composition that is centrifugally cast, and which when cured becomes rigid but not completely polymerized and therefore capable of being subsequently remolded with finger pressure when elevated in temperature. In this manner the adjustable frame portion is remoldable and conformable to desired portions of the oral cavity in the creating of an artificial denture, and the rigid frame portion formed from the first composition concurrently remains fixed as the adjustable frame portion is remolded.

23 Claims, 27 Drawing Figures

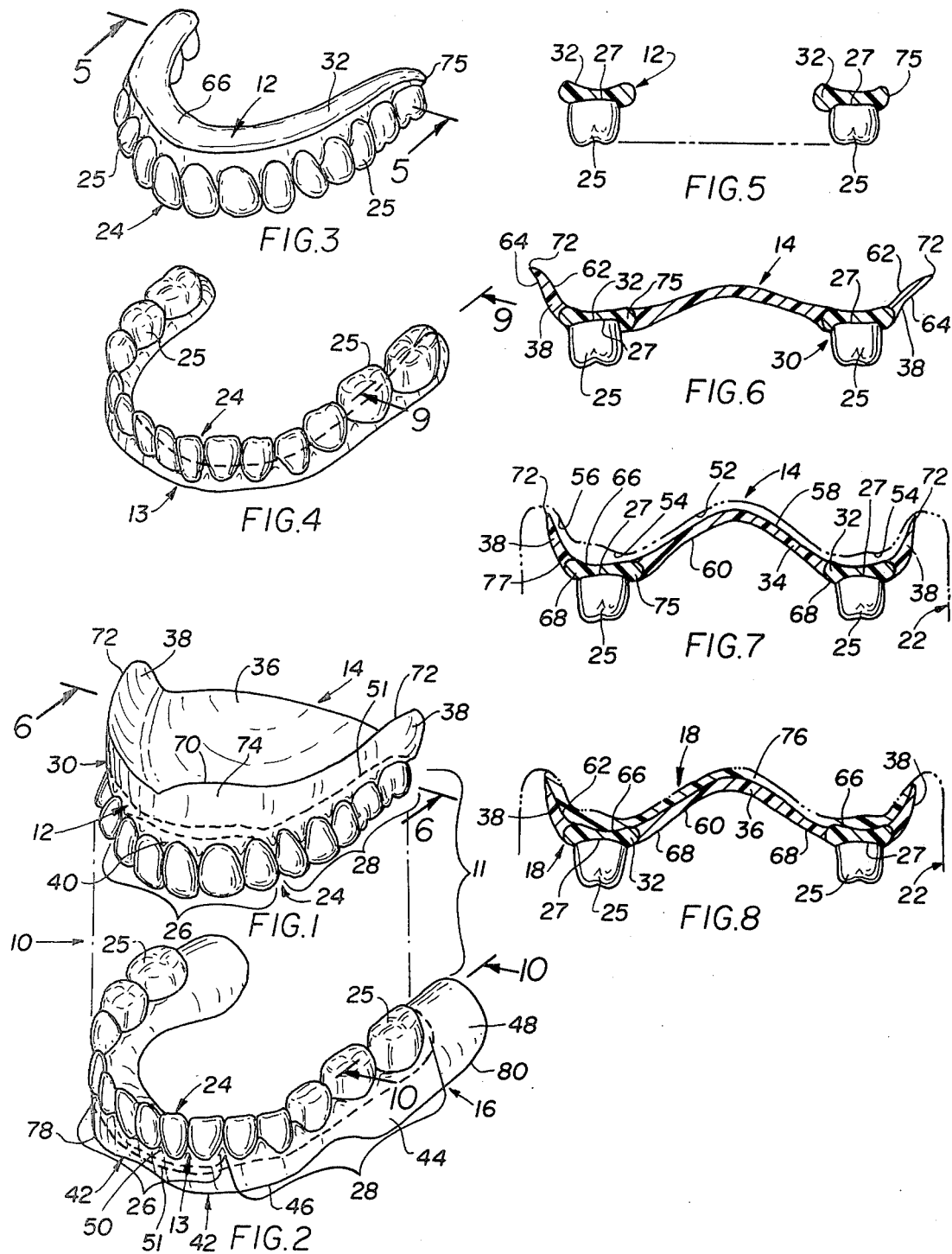

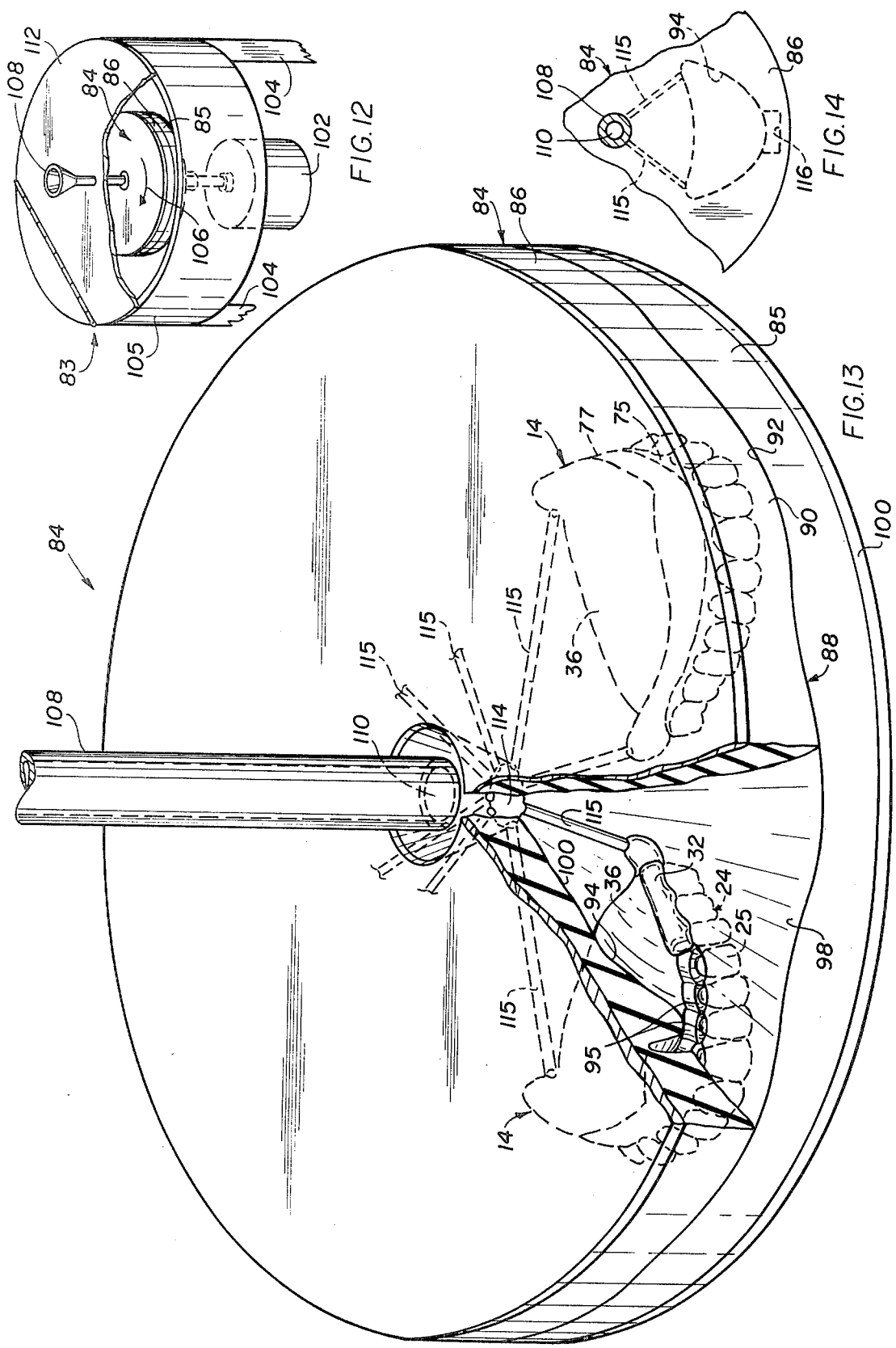

DENTURE AND ARTICLE FOR MAKING SAME

CROSS REFERENCE TO RELATED APPLICATION

This is a division of application Ser. No. 840,154 filed Oct. 7, 1977, now U.S. Pat. No. 4,161,065 issued July 17, 1979.

This application is related to the concurrently filed co-pending patent application of the same inventor, Ser. No. 840,156 filed Oct. 7, 1977, now abandoned which entire subject matter of the co-pending appication is incorporated herein by reference as if fully set forth herein.

BACKGROUND OF THE INVENTION

1. Field of the Invention

The present invention relates to an article or assembly for use in creating artifical dentures, and more particularly of the type that the dental profession may adapt to the patient's mouth at a single sitting if desired.

2. Description of the Prior Art

There are many people who have lost their natural teeth and who, for economic and other reasons, are unable to obtain prosthetic or artifical denture replacements through the services of professional dentistry. It has been appreciated in the prior art that the time and costs associated with providing a set of dentures to a patient could be substantially reduced if a portion of the artificial or prosthetic denture was previously manufactured and the final fitting to the patient's mouth took place during one or two dental visits. By providing to the dental profession an article that has been previously manufactured on a mass production basis, and that only requires a final fitting to a respective patient, the advantages and cost savings of a mass produced product can be passed along to the patient.

One form of prior art device is illustrated in U.S. Pat. No. 3,727,309, issued to Elbert P. Huey, and discloses a denture having certain characteristics to permit the dentist or other trained technician to perform certain adjustments while the denture is situated within the oral cavity of the prospective denture user. Huey appreciates that an assembly having a rigid structure to support the teeth and a flexible portion which could be deformed by finger pressure would permit the necessary adjustment to the curvature or configuration of the edentulus ridge in the maxillary area of the patient's mouth, for example.

The present inventor has found that the chemical composition selected in accordance with the teachings of U.S. Pat. No. 3,727,309 are such that resilient material utilized in the palatal vault area, for example, is readily softened upon exposure to temperatures that may occur in the mouth of the wearer of the dentures. This creates a problem in that if hot coffee is consumed, which may have a temperature to exceed 150° F., then there is a movement and there is a geometry change of the previously set palatal area of the maxillary denture.

The present inventor has discovered that by the utilization of certain chemical compositions it is possible to form a frame assembly having integrally joined portions, one of which always remains rigid and the other upon adjustment thereafter remains substantially rigid even when the wearer is consuming liquids of approximately 150° F. This feature provides a major advantage in the denture art over the device disclosed in U.S. Pat. No. 3,727,309.

Another form of prosthetic denture is disclosed in U.S. Pat. No. 3,839,796, issued to James M. Hazar, and discloses a denture to be individually fitted to the patient's mouth with a minimum of time involvement by the dentist. The present inventor has found that substantial improvement is obtained over the invention disclosed in U.S. Pat. No. 3,839,796 by providing a palatal vault member which when brought into conformable relationship with the palatal vault of the patient remains set in its selected position even when subsequently exposed to conventional elevated temperatures.

In the Hazar patent a palatal member is initially pressure molded having a specific configuration. This configuration is subsequently reheated by the dentist or other licensed denture delivery person, to remold the palatal member to conform to the palatal portion of the patient being fitted with dentures. It has been found that the palatal vault member manufactured in accordance with the teachings of U.S. Pat. No. 3,839,796 has a memory to it such that when subsequently subjected to heated liquid above 150° F., there is a softening thereof. Hot coffee can exceed 150° F. Accordingly, upon this reheating, the palatal vault member desires to return to its original configuration, and this has proven to be a drawback to the denture disclosed in Hazar U.S. Pat. No. 3,839,796.

The present invention should not be confused with the disclosure in U.S. Pat. No. 2,685,133, issued to B. N. Greene et al, in which the inventors' desire to provide a system wherein the individual who is remote from a dentist may perform those steps necessary to obtain the impression required to manufacture the dentures.

The present invention is adapted to provide the dentist with a greater degree of flexibility in producing a denture for the patient, and the various advantages and distinctions of my invention over the prior art will become more clearly evident as the disclosure proceeds.

In addition, up to the present invention the method and apparatus of manufacturing prosthetic devices to form artificial dentures have essentially been along coventional lines as that associated with dental laboratory procedures well known in the art. These procedures have been most satisfactory when producing individual sets of customized dentures, but they are not economically feasible for large production runs. The present invention also sets forth a method and apparatus for manufacturing large production runs of denture assemblies in an efficient and economical manner.

OBJECTS OF THE INVENTION

An object of the present invention is to provide an article for use in creating a denture which can be fitted by the dentist in a minimum of time, avoiding delays due to frequent fitting appointments with the patient.

Another object of the present invention is to provide a novel article for use in producing a prosthetic denture and methods and apparatus of manufacturing the article and prosthetic denture.

Another object of the present invention is to provide a prosthetic denture which includes an article having a frame assembly with a set of teeth extending therefrom in dentally operative position and the frame assembly having an adjustable frame portion which may be remolded by the dentist.

Another object of the present invention is to provide an article for use in creating a prosthetic denture device and a novel method and apparatus for spin casting of a chemical composition adjacent to a set of teeth previously positioned in a mold for producing the article.

Other objects and advantages of the present invention will become apparent as the disclosure proceeds.

SUMMARY OF THE INVENTION

The outstanding and unexpected results obtained by the practice of the method and appartus of this invention are obtained by a series of features, steps and elements assembled and working together in interrelated combination.

In accordance with one aspect of the present invention, an article for use in creating a prosthetic denture device is formed of a set of hard teeth bonded within a frame assembly formed of a permanent substantially rigid hard frame portion having the set of teeth extending therefrom in dentally operative position. The rigid hard frame portion being formed from a first composition which when cured becomes polymerized so as to remain rigid and not subsequently deformable.

An adjustable frame portion is integrally joined to the rigid frame portion and forms part of the frame assembly and is formed from a second composition which when cured becomes rigid but not completely polymerized and therefore capable of being subsequently remolded with finger pressure either at or above room temperature. In this manner the adjustable frame portion is remoldable and conformable to desired portions of the oral cavity in the creating of an artificial denture, and the rigid frame portion formed from the first composition concurrently remains fixed as the adjustable frame portion is remolded.

The novel article and denture of the present invention is fabricated by placing a set of artifical teeth in a mold having a spaced continuous cavity along the base portion of the teeth and selecting a first composition having the properties which when cured is polymerized so as to remain rigid and not subsequently deformable. Further, by selecting a second composition having the properties which when cured becomes rigid but is not completely polymerized, the second composition is therefore capable of being subsequently remolded with finger pressure when elevated in temperature.

By filling selective portions of the cavity with the first composition and the second composition, and then curing both compositions in the cavity, they are integrally joined together. In this manner it is possible to obtain a rigid frame assembly or structure from which the teeth depend, whereby in producing the artificial denture the portion of the frame assembly fabricated from the second composition is remoldable when elevated in temperature by finger pressure to closely conform the second composition to desired portions of the oral cavity and the rigid frame portion comprised of the first composition concurrently remaining rigid.

The apparatus for manufacturing an article used in dentistry, such as an artificial denture of the like, in accordance with the present invention, includes a mold separable into two sections and having at least one cavity therein. A set of artificial teeth are supported in the cavity in a dentally operative relationship to each other, and means for rotating the mold with the set of artificial teeth positioned therein is provided. In addition means for providing access to the cavity as the mold is rotating so as to cause a flow of a material into the cavity such that a centrifugally cast frame is formed with the teeth depending therefrom is also provided. The rotating of the mold is at approximately 675 R.P.M., and the mold includes a plurality of individual cavities connected from a substantially central position such that a centrifugal casting of one frame in each of the cavities is formed.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 1 is a perspective view illustrating a maxillary article for use in creating a set of prosthetic dentures in accordance with the present invention;

FIG. 2 is a perspective view illustrating a maxillary and mandibular article for use in creating a set of prosthetic dentures in accordance with the present invention;

FIG. 3 is a perspective view of a maxillary upper frame as it is initially fabricated in the manufacture of a maxillary article;

FIG. 4 is a perspective view of a mandibular frame as it is initially fabricated in the manufacture of a mandibular article;

FIG. 5 is a sectional view taken along line 5—5 of FIG. 3;

FIG. 6 is a sectional view taken along lines 6—6 of FIG. 1 illustrating the maxillary article prior to positionment in the oral cavity;

FIG. 7 is a view similar to FIG. 6 illustrating the change of contour of the palatal vault area and the tuberosity heels to be brought into conformal relationship with the edentulus ridge in the maxillary area of the patient's mouth;

FIG. 8 is a view similar to FIG. 7 illustrating the application of a liner to the upper surface of the maxillary article to form a prosthetic denture;

FIG. 12 is a perspective view of apparatus in accordance with the present invention for centrifugal casting of denture related articles in accordance with the present invention;

FIG. 13 is an enlarged perspective, partly broken away and in section, illustrating the separable sections of the mold in which the articles are formed;

FIG. 14 is an enlarged fragmentary top plan view illustrating the flow of material to each cavity in the mold;

DESCRIPTION OF PREFERRED EMBODIMENT

Figure 15:
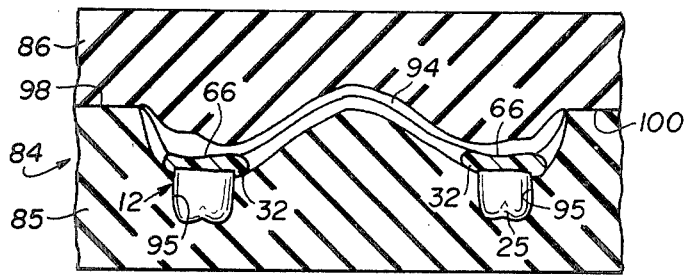
FIG. 15 is a cross-sectional view of the mold assembly illustrated in FIG. 13, utilized in the fabrication of a maxillary denture.

Referring to the drawings in detail, there is illustrated in FIGS. 1 through 20 the procedure and apparatus for both fabricating and converting one or more articles 10 into a set of prosthetic dentures 11. To form the dentures 11 there is initially fabricated a maxillary or upper frame 12 and a mandibular or lower frame 13. The articles 10 include a maxillary or upper denture article 14 and a mandibular or lower denture article 16, which may be subsequently processed, in a manner hereinafter described, to form a maxillary or upper denture device 18 and a mandibular or lower denture device 20. The novel construction of the articles 14 and 16 permits selective adjustment of portions thereof to provide a customized fit to the contour of the oral cavity 22 of a particular patient.

The maxillary article 14 is comprised of a set 24 of hard teeth which may be cast or molded from a acrylic resin. Other resins are also suitable, provided they have the necessary combination of properties as hardness, stain resistance, impact strength, non-flow (non-creep) and resistance to body fluids and foods. They must also be non-toxic and non-irritating to membranes and have color stability. A set of teeth 24 is associated with articles 14 and 16 and include individual teeth 25. Each set 24 is divided into an anterior group or segment 26 and a posterior group or segment 28. Each tooth 25 has a base portion 27 which is embedded or contained below the exposed surface of the denture articles 14 and 16. A set of teeth 25 in accordance with the present invention, may include only an anterior group 26, posterior groups 28, or both groups.

Article 14 is to be utilized in creating a maxillary prosthetic denture device which is readily fitted in a customized fashion to the oral cavity 22 of the patient. Although the article 14 may be manufactured in various sizes such as small, medium and large, as well as tapered or oval configurations, it is necessary to select an article and remold certain portions thereof in order to obtain the customized fit desired.

Accordingly, the set 24 of hard teeth is contained in a frame assembly 30 that is comprised of the upper frame 12, and includes portion 32 into which all, or substantially all, of the teeth 25 may be contained. The set of teeth 24 is positioned in dentally operative relation to each other. Separate portions of the frame assembly 30 are designed to act as an adjustable frame portion 34. The adjustable frame portion 34 is integral with the rigid frame portion 32 forming part of the upper frame 12. As illustrated in FIG. 1, the palatal vault area 36, as well as the tuberosity heels 38, have been fabricated from the adjustable frame portion 34. In addition, the anterior portion 40 of the frame assembly 30 may be also seated within an adjustable frame portion 34.

In this manner with respect to the maxillary article 14, one or more sections thereof may be fabricated from an adjustable frame portion 34 which, as hereinafter explained, is conformable to selective areas of the oral cavity 32. Preferably the upper frame 12 is fabricated from a rigid plastic or other material and a full or partial set of teeth 25 are rigidly connected thereto. The adjustable frame portion 34 preferably constitutes the balance of the maxillary article 14, although only selective portions may be fabricated from an adjustably deformable material.

The construction of the mandibular denture 18 may be similarly constructed of a lower frame 13 and an adjustable portion integrally formed therewith. The mandibular article 16 may be similarly formed such that a frame assembly 42 has contained therein a set of teeth 24 that is contained in the lower frame 13. The set of teeth 24 may be divided into an anterior segment 26 and a posterior segment 28 extending on each side thereof. The frame assembly 42 is comprised of the lower frame 13 which includes a rigid hard frame portion 44 into which all of the teeth 25 may be set. In addition, an adjustable frame portion 46 is provided and formed integral with the rigid frame portion 44. The retromolar pad areas 48, as well as other portions of the denture article 16, may be selected to be fabricated from the adjustable frame portion 46.

In addition, the anterior portion 50 may also be fabricated from an adjustable frame portion 46. It is appreciated that the exact outline and area of junction indicated by broken lines 51, between the rigid frame portions 32 and 44, and adjustable frame portions 34 and 46, respectively, may vary considerably. Accordingly the areas outlined by the broken lines 51 are merely indicative of those portions of the frame assemblies 30 and 42 that most often require adjustment in the fabrication of the dentures 18 and 20. As illustrated in FIGS. 6 through 8, the maxillary article 14 is to be brought into conformal relationship with the palatal vault area 52, toothless human gum area 54, and tuberosity heel portion 56.

The palatal vault area 36 includes the upper or inner surface 58 and a lower or outer surface 60. Similarly, the tuberosity heels 38 include an inner or upper surface 62 and a lower or outer surface 64. The rigid frame portion 32 is similarly provided with an upper or inner surface 66 and a lower or outer surface 68 from which the set of teeth 24 extends downwardly in a generally U-shaped configuration.

The surface 66 is adapted to generally receive the toothless gum area 54 of the oral cavity 22. The frame assembly 30 includes an upper terminal edge or ridge 70 which may blend with the upper terminal edge or ridge 72 of each of the tuberosity heels 38. The upper terminal edge 70 defines the upper extremity of the vertically extending wall portion 74 which extends upwardly from the set of teeth 24 and the rigid frame portion 32.

In accordance with the present invention the rigid frame portion 32 of the maxillary article 14, and the rigid frame portion 44 of the mandibular article 16, are selected to be formed from a first composition 75 which when cured becomes polymerized so as to remain rigid and not subsequently deformable. In this manner upon curing of the frame assembly 30 and 42, there is provided a rigid hard base structure 32 into which the set of teeth 24 may be permanently set in a dentally operative position.

To provide the necessary adjustability, the adjustable frame portions 34 and 46 are formed from a second composition 77 which when cured becomes rigid but not completely polymerized and therefore capable of being subsequently remolded with finger pressure either at room temperature of when elevated to a select temperature.

Furthermore, upon cooling the adjustable frame portions 34 and 46, if the second composition 77, is moldable at above room temperature, it becomes rigid and moldable if subsequently raised to the initial elevated temperature. The plastic materials advantageously used in the first composition 75 and second composition 77, to obtain the novel denture articles 14 and 16, are hereinafter described in detail.

With particular reference to FIG. 7, the maxillary article 14 has now had the adjustable frame portion 34, particularly the palatal vault portion 36 and tuberosity heels 38, contoured to a desired configuration. The second composition 77 is selected from plastic material which when elevated in temperature, as by placing in liquid such as water in the temperature range of 160° F. to 212° F., will cause a softening of the adjustable frame portion 34 to occur. This step may be carried out exteriorly of the oral cavity 22, in that the dentist may first view the contour of the oral cavity 22 and conform the palatal vault area 36 and tuberosity heels 38 to a desired contour. In addition the vertically extending wall portion 74 is also adjustable.

In this manner the first step of forming the article 14 into the maxillary denture 18 occurs in that the palatal vault area 36 becomes resilient at a temperature which is preferably about 180° F. and capable of being set in a reformed position from that as shown in FIG. 6. After the article 14 is cooled, as by quenching in cold water, the adjustable frame portion 34 becomes rigid.

In this manner the platal vault area 36, formed from the adjustable frame portion 34, may be deflected upwardly into various positions depending upon the geometry of the palatal vault of a given patient. Since the preferred temperature for the second composition to be deformed is approximately 180° F., the finger pressure by the dentist is generally applied when the article 14 is not within the mouth of the patient. Upon cooling of the palatal vault area 36, tuberosity heel areas 38 and wall portion 74, they will remain in a set position in close conformity with the geometry of the respective oral cavity 22.

Accordingly the adjustable frame portions 34 and 46 are formed from the second composition 77, which becomes rigid when cured but not completely polymerized, and therefore capable of being subsequently remolded with finger pressure when elevated in temperature. In this manner the adjustable frame portions 34 and 46 are remoldable and conformable to desired portions of the oral cavity 22 in the creating of an artificial denture, and the rigid frame portions 32 and 44 are formed from the first composition 75, which concurrently remains fixed as the adjustable frame portions 34 and 46 are remolded.

The novel set of articles 10 require in the manufacturing thereof the selecting of the first composition 75, having the properties which when cured becomes polymerized so as to remain rigid and not subsequently deformable, and selecting the second composition 77 having the properties which when cured becomes rigid but is not completely polymerized.

Therefore the second composition 77 is capable of being subsequently remolded with finger pressure when elevated in temperature, and upon cooling becoming substantially rigid, but thereafter moldable if subsequently raised to a preselected elevated temperature. In this manner several adjustments of the adjustable frame portions 34 and 36 may take place until the desired fit for a particular patient is obtained.

As illustrated in FIG. 8, the final fitting of the maxillary article 14 occurs in that a liner 76 of plastic material, well known in the art, is applied to the contiguous upper surfaces 58, 62 and 66. The liner 76 is of a relatively soft material until cured, so that it very accurately conforms with the features of the maxillary surfaces 52, 54 and 56 of the oral cavity 22.

The maxillary article 14, as illustrated in FIGS. 1 and 6, now has a recontoured configuration, as illustrated in FIG. 8. These changes in contour may be in one or more areas, for example the palatal vault area 36 and the tuberosity heels 38. When the liner 76 is formed on the upper surfaces 58, 62 and 66, the resultant maxillary denture 18 is now fabricated and ready to be worn by the user.

It has also been found that in certain instances it is desirable to have the ability to alter the exact alignment or positionment of one or more of the teeth 25 forming the anterior segment 26. In accordance with the present invention, this ability is provided by molding the anterior segment 26 within an anterior portion 50 fabricated from the second composition 77 so as to form an adjustable frame portion 40.

At such time as the denture article 14 is elevated in temperature, the teeth 25 forming the anterior portion 26 may be changed as to their positionment relative to each other, or they may be left in the exact position as they are initially manufactured. This permits additional flexibility to customize the dentures 18 and 20 produced in accordance with the teachings of the present invention.

Figure 9:
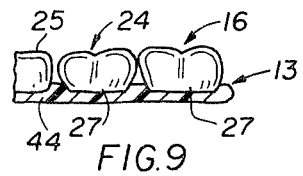
FIG. 9 is a sectional view taken along lines 9—9 of FIG. 4.
Figure 10:
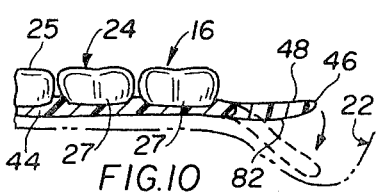
FIG. 10 is a sectional view taken along lines 10—10 of FIG. 2, illustrating the change of contour of the retromolar pad area as it is brought into conformal relationship with the area of the patient's mouth.
Figure 11:
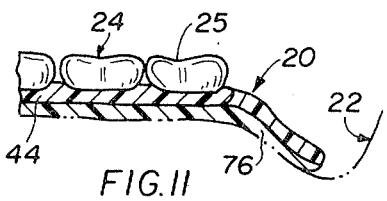
FIG. 11 is a view similar to FIG. 10 illustrating the application of a liner to the surface of the mandibular article to form a prosthetic denture.

FIGS. 9 through 11 illustrate the progressive steps of custom fitting the article 16 so as to form the mandibular denture 20 having a liner 76 thereon to fit the human gum area. The mandibular article 16 terminates in a free end 78 that merges with the outer or free end 80 of the retromolar pad areas 48. It has been found that the retromolar pad areas 58, having an inner or upper surface 82, generally require adjustment relative to the associated area of the oral cavity 22. As illustrated in FIG. 10, the retromolar pad area 48 may be reformed to a desired configuration. This is accomplished during the period of time that the mandibular article 16 is raised to an elevated temperature such that the second composition 77, hereinafter discussed in detail, is raised to the requisite temperature in order to remold same with finger pressure. The remolding may occur when the mandibular article 16 is contained exteriorly of the oral cavity 22.

As illustrated in FIG. 11, the liner 76 is thereafter applied in its soft uncured state to obtain the final fitting over the mandibulary ridge of oral cavity 22, in order to form the mandibular denture 20. In this embodiment the anterior segment 26 may similarly be set in an anterior portion 50 fabricated from material of the second composition 77. As explained with respect to the maxillary denture 18, this permits selective positioning of the individual teeth 25 contained in the anterior segment 26.

The manufacturing process as to produce the articles 14 and 16 in accordance with the present invention may be varied, but a preferred form of equipment is illustrated in FIGS. 12 through 20. FIGS. 12-14 illustrates a preferred form of apparatus 83 for centrifugal casting of the second composition 77 to form the complete frame of either the denture article 14 or 16. The apparatus 83 utilizes a mold or mold assembly 84 which has a lower mold or section 85 and an upper mold or section 86 with aligning means 88, which may be in the form of individual elements 90 adapted to be received in wells 92. The lower mold 85 may include a continuous cavity 94 with means for supporting the individual teeth therein, such as pockets or recesses 95 adapted to receive a set 24 of the individual teeth 25 therein. The cavity 94 extends below the upper surface 98 of the lower mold 85 and may also extend within the upper mold 86, above the lower surface 100 thereof. Each tooth 25 has its base portion 27 that extends within the cavity 94. The molds 85 and 86 may be fabricated from silicone rubber or other similar materials, but yet having a certain degree of flexure, in order to permit the undercut portions of cavity 94 to have the contained portions of article 14 therein removed therefrom. It is appreciated that molds may be used of metal or other materials provided that removal of a cured article 14 or 16 may be removed therefrom. Certain plastic compositions may also be used.

Figure 16:
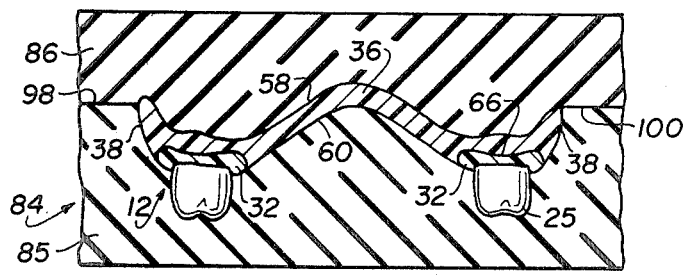
FIG. 16 is a sectional view similar to FIG. 15 illustrating the flow of a second composition within the cavity of the mold by centrifugal casting.
Figure 18:
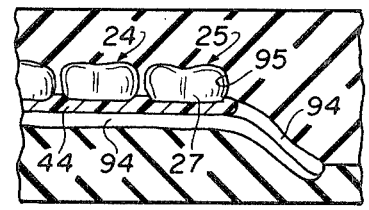
FIG. 18 is a cross-sectional view of the mold assembly illustrated in FIG. 13, when utilized in the fabrication of a mandibular denture.
Figure 17:
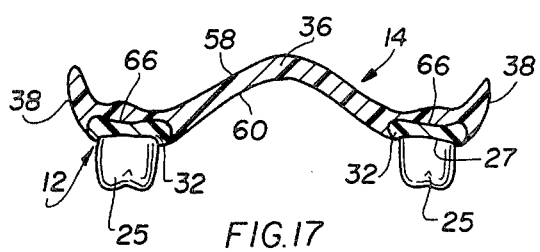
FIG. 17 is a sectional view of the maxillary denture as it is removed from the mold.
Figure 19:
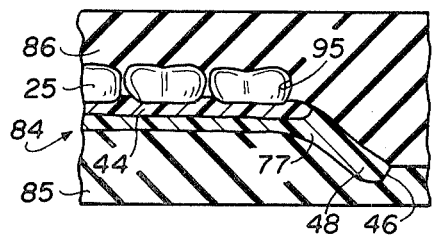
FIG. 19 is a sectional view similar to FIG. 18 illustrating the flow of a second composition within the cavity of the mold by centrifugal casting.
Figure 20:
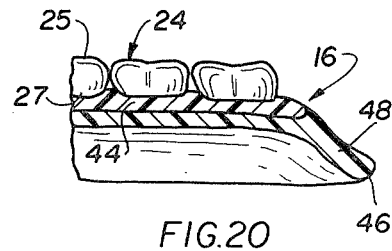
FIG. 20 is a sectional view of the mandibular denture as it is removed from the mold.

Although a maxiilary article 14 is illustrated with respect to the manufacturing procedures illustrated in FIGS. 13, 15 and 16 a mandibular article 16 may be fabricated in a similar manner as illustrated in FIGS. 18 through 20.

With particular reference to FIG. 15, there is illustrated the method of fabricating the article 14 by utilizing the molds 85 and 86 and placing the set 24 of artificial teeth 25 along the sockets 95 provided therefor. In this embodiment the upper frame 12 produced with the first composition 75, which is to form the rigid frame portion 32 of the frame assembly 30, may be initially fabricated as a subassembly outside of the mold assembly 84 and inserted therein prior to casting the second composition 77. In the alternative the teeth 25 may be first positioned in the recesses 95 and the first composition 75 poured or positioned on the teeth 25 while the teeth 25 are contained in the mold assembly 84.

The second composition 77, which is to form the adjustable frame portion 34, which may include the palatal vault area 36, tuberosity heels 38 and wall portion 74 are formed by filling selective portions of the cavity 94 concurrently. The viscosity of the second composition 77 is such that it may selectively flow into respective portions of the cavity 94.

In this manner the complete article 14 is such that a curing operation may take place with the mold assembly 84, to integrally join the compositions in order to form the desired frame assembly 30. The curing of the first and second compositions in the mold 84 may take place at room temperature or at a temperature of approximately 212° F. At the elevated temperature the initially rigid frame assembly 30 is produced with only the adjustable portion 34 readily remoldable with finger pressure and conformable to the oral cavity of the person's mouth as the first composition 75 concurrently remains rigid.

In this manner by properly selecting the first and second compositions 75 and 77, respectively and subsequently curing same while situated in the mold 84, it is posible to form a maxillary article 14 which is subsequently formed into a complete denture, as previously described with respect to FIGS. 6 through 8. It is appreciated that the anterior portion 50 may be concurrently formed in the mold 84 to obtain the end result illustrated in FIGS. 1 and 2 if so desired.

The first composition 75 which forms the rigid frame portion 32 of the maxillary article 14 and the rigid frame portion 44 of the mandibular article 16 is a polyacrylic thermoplastic material formed by curing a viscous mixture of a polyacrylic powder and a liquid acrylic monomer.

The polyacrylic powder can be a homopolymer of methyl methacrylate or a mixture of a homopolymer of methyl methacrylate and a copolymer of methyl methacrylate and ethyl methacrylate. Generally the copolymer portion should contain an excess of combined methyl methacrylate over combined ethyl methacrylate. Copolymers containing about 70% combined methyl methacrylate and 30% combined ethyl methacrylate are preferred.

The liquid acrylic monomer is preferably liquid methyl methacrylate monomer, which liquid monomer may also contain one or more cross-linking agents and activators such as benzoyl peroxide as well known in the art. Other liquid acrylic monomers such as ethyl methacrylate may also be employed.

In preparing the first composition, the powder is added to the liquid to form a handleable paste. The volume ratio of powder to liquid to form the rigid frame portions 32 and 44 of frame assemblies 30 and 42 respectively is 3:1 or a weight ratio of powder to liquid of 2:1. The paste may then be cured at between five minutes and thirty minutes to form a rigid thermoplastic.

The first composition exhibits the characteristics in that during the curing stage it becomes rigid and thereafter does not become viscous or softened unless raised to temperatures well beyond that normally encountered by the wearer of the dentures, i.e., above 212° F.

The second composition is formed from a heat-curable mixture of a polyacrylic powder and a plasticized liquid acrylic monomer. This composition when cured, becomes rigid, but not completely polymerized, and is therefore capable of being subsequently remolded with finger pressure at moderately elevated temperatures. The polyacrylic powder is the same as the polyacrylic powder used in connection with the first composition discussed above.

The plasticized liquid acrylic monomer used in forming the second composition comprises a liquid acrylic monomer and a liquid plasticizer mixture. The acrylic monomer is preferably methyl methacrylate although other dental grade acrylic monomers may also be employed. The plasticizer mixture may comprise one or more liquid plasticizers, selected from the group consisting of dibutyl phthalate, butyl benzyl phthalate, dimethyl phthalate, dicyclohexyl phthalate, diisodecyl phthalate, dioctyl phthalate, butyl phthalyl butyl glycolate, isodecyl diphenyl phosphate, alkyl benzyl phthalate, and mixtures thereof.

A suitable formula for the plasticizer mixture has also been found to comprise from about 45 to 55 weight percent of N-ethyl o, p-toluenesulfonamide, from about 11 to 17 weight percent of dimethyl phthalate, from about 11 to 17 weight percent of butyl phthalyl butyl glycolate, from about 4 to 10 weight percent of diisodecyl phthalate, from about 6 to 14 weight percent of octylene glycol and from about 1 to 4 weight percent of polyester resin. More specifically this combination of the composition comprises 52 weight percent of said N-ethyl o, p-toluenesulfonamide, 14 weight percent of said dimethyl phthalate, 14.5 weight percent of said butyl phthalyl butyl glycolate, 7.0 weight percent of said diisodecyl phthalate, 1.0 weight percent of said octylene glycol, and 2.5 weight percent of said polyester resin.

The plasticized liquid acrylic monomer comprises from about 30 to 40 parts by weight of acrylic monomer and from about 70 to 10 parts by weight of plasticizer mixture. Preferably the plasticized liquid acrylic monomer comprises about 75 parts by volume monomer and 25 parts by volume plasticizer mixture. The ratio of 70 to 30 has also been found suitable. The plasticizer liquid may also contain an activator such as benzoyl peroxide and crosslinking agents.

The above liquid can be prepared by concentrating a diluted plasticized liquid acrylic monomer with additional acrylic monomer until a liquid is obtained having the desired weight range of acrylic monomer and liquid plasticizer described above.

One such diluted liquid is sold under the commercial name "Tru-Soft" by the Harry J. Bosworth Company of Chicago, Illinois. This liquid contains about 200 parts by weight of methyl methacrylate monomer and 2,000 parts by weight of plasticizer which converts to about 9% monomer.

In preparing the second composition, the powder is added to plasticized liquid acrylic monomer to form a paste. The volume ratio of powder to liquid should be about 3:1. The paste can then be cured at temperatures between 165° F. and 212° F. for 20 minutes to 30 minutes.

The second composition formed from these materials is such that it may be integrally formed with the first composition such that there is no visual distinction between the respective areas or portions of the denture frame assemblies 30 and 42. Further, the reaction of the second composition is based upon the application of heat. When the denture article 14 and 16 is heated, as by placing in liquid such as water having a temperature in the range of 160° F. to 212° F., and preferably about 180° F., there is a reaction and most of the residual plasticizers and monomers in the second composition are driven off from the system and the second composition goes into a stable state and cannot then be remolded without reheating.

Depending upon the mixture of the fluid forming the second composition, the adjustable frame portions 34 and 46 may be deformed one or more times before a final setting is reached. Due to the temperature at which the second composition is deformable, which is approximately 180° F., the dentist would first place the article 14 or 16 in heated water such that the adjustable frame portions 34 and 46 soften to the point where they are remoldable by finger pressure. The dentist would remold these portions such as the palatal vault area 36, tuberosity heels 38, or retromolar pad areas 48, after visually inspecting the oral cavity to determine the amount of adjustment required.

The second composition is so selected such that after cooling of the article 14 or 18, the dentist fits the remolded article into the patient's mouth to check the quality of the fit after remolding. If a second adjustment is required, the process may then be repeated a second or third time so as to obtain a closer adjusted fit.

Further, the second composition has basically no "memory" in that there is no tendency for it to return to an original configuration, which is a deficiency with dentures formed by the prior art teachings. The liner 76, which may be fabricated from impression materials well known in the dental art, is then poured over the upper surfaces of the article 14 or 16 and the final impression is made. The liner 76 is curable by conventional dental procedures.

FIGS. 12 through 14 illustrate the spin casting apparatus 83 that may be utilized to obtain the completed denture articles 14 or 16. Prior to the utilization of apparatus 83, considerable amounts of hand labor were required in order to obtain the finished product. The ability to utilize the product 10 has considerably advanced the art and provides a technical breakthrough in the manufacture of denture components. The apparatus 83 is such that the mold sections 85 and 86 may be fabricated from silicone rubber and are produced so that they may withstand usage over prolonged periods of time.

The frame assembly 12 or 13 may be fabricated earlier and inserted within the lower section 85, prior to positioning the upper section 86, in overlapping relationship thereto utilizing the aligning means 88. The mold assembly 84 may then be positioned within the apparatus 83 on a table 100 which is adapted to be rotated at a speed of approximately 675 RPM by a motor 102. The apparatus 83 includes a plurality of legs 104 and a frame 105 which has the mold assembly 84 positioned therein.

As the table 100 is rotated, as indicated by arrow 106, the second composition 77 is continuously poured through a funnel 108 into the mold assembly 84 through a center opening 110 in the top 112 of the casting machine 83. The plastic second composition 77 flows, by gravity, into the center sprue 114 and through the runners 115 in the mold assembly 84 to the individual cavities 94. Spin cycle time is determined according to the characteristics of the second composition 77. It has also been determined that the curing of the denture article 14 or 16 may take place within the mold assembly by utilization of a self-curing type of material which forms part of the second composition 77. In this manner, at the end of the spin cycle, which may vary from several to thirty minutes, the denture article 14 or 16 is completely cured and ready to be packaged for shipment. Obviously, any flash as well as the runners are removed in a conventional manner.

Although four cavities 94 are easily filled simultaneously, it is appreciated that more or less may be utilized in each mold assembly 84. It has been found preferable that two runners 115, as illustrated in FIG. 14, be utilized to obtain an equalized centrifugal flow of the second composition 77 within each cavity 94. There may also be provided an enlarged area or pocket 116 into which escaped air may flow.

The resultant product 14 or 16 does not require further polishing, which has in prior processes resulted in extensive hand labor which appreciably increased the cost of the product and further was deleterious as to the appearance thereof.

Figure 22:
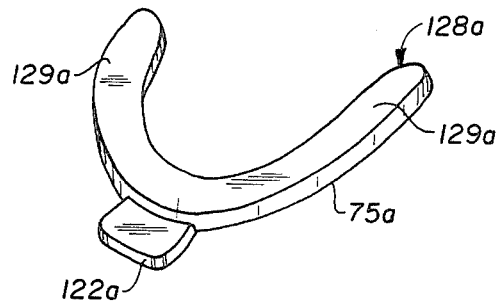
FIG. 22 is a perspective view of the first frame which forms part of the impression tray illustrated in FIG. 21.
Figure 21:
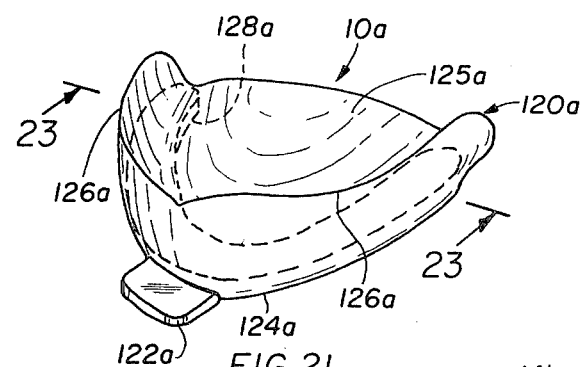
FIG. 21 is a perspective view of an impression tray which may be manufactured in accordance with the present invention.
Figure 23:
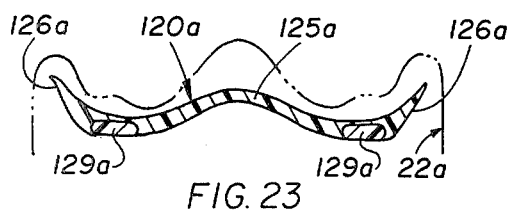
FIG. 23 is a sectional view taken along lines 23—23 of FIG. 1 illustrating the impression tray positioned within the oral cavity prior to adjustment of the configuration of any portions thereof.
Figure 24:
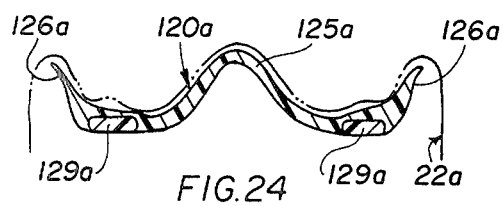
FIG. 24 is a view similar to FIG. 23 illustrating the impression tray with the contour of certain portions thereof having been changed.
Figure 25:
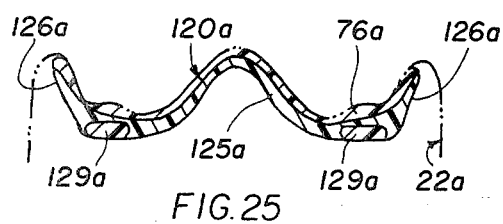
FIG. 25 is a view similar to FIG. 24 with a hard impression liner on the impression tray.

FIGS. 21 through 25 illustrate a denture article 10a that is in the form of an impression tray 120a which may be manufactured with the apparatus illustrated in FIGS. 12 through 14. The impression tray includes a handle 122a formed at one end thereof and which is formed from the first composition 75. The impression tray 120a has a frame assembly 124a that includes a U-shaped bottom wall 125a and upwardly extending side walls 126a. The rigid frame portion 128a is illustrated in FIG. 22 and has a pair of legs 129a joined together. The frame assembly 124a is integrally formed with the side walls 126a and the bottom wall 125a. The side walls 126a and bottom wall 125a may be fabricated from the second composition 77a. In this manner the user of the impression tray 120a can elevate its temperature and the side walls 126a and bottom wall 126a can be altered in contour since they are fabricated from the second composition 77a. In this manner the utilization of the impression tray 120a, as illustrated in FIGS. 23 through 25, can take place by the user. The impression tray 120a is elevated in temperature as described above and the portion thereof fabricated from the second composition 77a may easily be contoured relative to the shape of the oral cavity 22a as illustrated in FIG. 24.

As illustrated in FIG. 25, the liner of impression material 76a is positioned in the tray 120a, and the dentist may take the desired impression in a conventional manner. Prior to this invention, impression trays were generally not adjustable, and therefore, the dentist was required to stock a considerably number of such trays. By the present invention a minimal number of different size trays can be utilized since they are readily adjustable and may be subsequently disposed of for sterility purposes.

Figure 26:
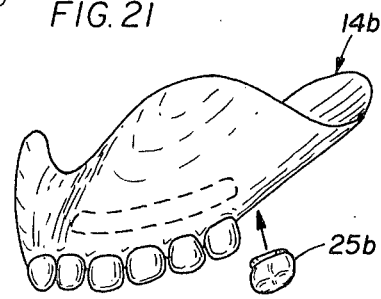
FIG. 26 is a perspective view of a maxillary denture in which the teeth are positionable thereon by the dentist.
Figure 27:
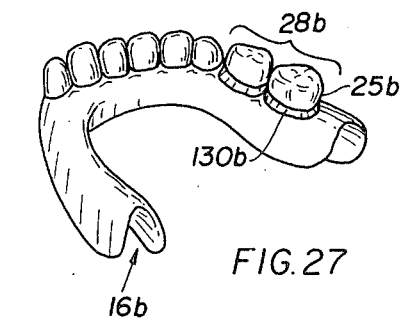
FIG. 27 is a perspective view of an mandibular denture in which certain teeth thereof are adjustable thereon.

As illustrated in FIGS. 26 and 27, it may be desirable to provide denture articles 14b and 16b in which the individual teeth 25b of the posterior group of teeth 28b are not positioned on the denture assembly 14b or 16b when intially fabricated. In all other respects the denture assembly 14b and 16b may be manufactured as described with respect to FIGS. 1 through 20. This permits the dentist to individually position, by using a wax material 130, or the like, to individually couple the teeth 25b to the denture assembly. In this manner individual positioning can be obtained by the dentist when using the product.

The denture articles illustrated herein may either be fabricated into a complete denture assembly, as illustrated in FIGS. 8 and 11 with a liner thereon, or they may be utilized in a manner which is called the "two step procedure". This procedure is such that the denture assembly with the impression therein is sent to a dental laboratory and by using conventional techniques the teeth of the denture article are "jumped", such that a newly formed denture using the impression previously taken is utilized to form a finalized product. In this manner a relining is obtained such that the second composition and the original rigid liner are substantially removed and replaced by in order to form a complete denture. The third composition is selected to be compatible with the first composition and conforming to the contour of the original rigid liner. There is then a curing of the third composition and the first composition in a conventional manner for creating a prosthetic denture. The denture components of the present invention are adaptable for either mode of operation.

Although illustrative embodiments of the invention have been described in detail herein with reference to the accompanying drawings, it is to be understood that the invention is not limited to the precise embodiments, and that various changes and modifications may be effected therein without departing from the scope or spirit of the invention.

I claim:

1. An article for use in producing a prosthetic denture device comprising
    a frame assembly comprised of (A) a rigid hard frame portion formed from a first composition comprising a cured mixture of a first polyacrylic powder and a liquid acrylic monomer and
    (B) an adjustable frame portion integral with said rigid frame portion, said adjustable frame portion formed from a second composition comprising a heat-curing ridgid mixture of a second polyacrylic powder and a plasticized liquid acrylic monomer which mixtured is rigid but not completely polymerized and therefore capable of being shaped with finger pressure, said plasticized liquid acrylic monomer comprising from 30% to 90% by weight of liquid acrylic monomer and from 70% to 10% by weight of a plasticizer mixture, wherein
    said adjustable frame portion is remoldable and conformable to desired portions of the oral cavity, and said rigid frame portion formed from said first composition concurrently remains fixed as said adjustable frame portion is remolded.

2. The article as defined in claim 1, wherein said article is in the form of an impression tray having a handle integrally formed at one end thereof, said handle being formed from said first composition.

3. The article as defined in claim 2, wherein said frame assembly has a substantially U-shaped configuration with a bottom wall and upwardly extending sidewalls.

4. The article as defined in claim 3, wherein said bottom wall forms said rigid hard frame portion and said side walls form said adjustable frame portion.

5. The article as defined in claim 1, in the form of a maxillary artificial denture having a palatal vault area thereon, said second composition forming said palatal vault area.

6. The article as defined in claim 5, wherein said article is formed having tuberosity heels formed from said second composition.

7. A prosthetic denture device comprising
    a frame assembly according to claim 1 having a set of hard teeth extending therefrom in a dentally operative position.

8. The article as defined in claim 7, wherein said second composition remains rigid within the temperature range that said first composition is remoldable.

9. The article as defined in claim 7, wherein said second composition is remoldable when elevated to a temperature in the range of 160° F. to 212° F.

10. The article as defined in clam 9, wherein said second composition is remoldable at approximately 180° F.

11. The article as defined in claim 7, wherein said first and second polyacrylic powders are each a homopolymer of methyl methacrylate or a mixture of a homopolymer of methyl methacrylate and a copolymer of methyl methacrylate and ethyl methacrylate.

12. The article as defined in claim 7, wherein the plasticized liquid acrylic monomer comprises about 35% by weight of liquid acrylic monomer and about 25% by weight of a plasticizer mixture.

13. The article as defined in claim 7, wherein said plasticizer mixture comprises from about 45 to 55 weight percent of N-ethyl o, p-toluenesulfonamide, from about 11 to 17 weight percent of dimethyl phthalate, from about 11 to 17 weight percent of butyl phthalyl butyl glycolate, from about 4 to 10 weight percent of diisodecyl phthalate, from about 6 to 14 weight percent of octylene glycol and from about 1 to 4 weight percent of polyester resin.

14. The article as defined in claim 13, wherein said plasticizer mixture composition comprises 52 weight percent of N-ethyl o, p-toluenesulfonamide, 14 weight percent of said dimethyl phthalate, 14.5 weight percent of said butyl phthalyl butyl glycolate, 7.0 weight percent of said diisodecyl phthalate, 10.0 weight percent of said octylene glycol, and 2.5 weight percent of said polyester resin.

15. The article as defined in claim 13, wherein said liquid acrylic monomer is methyl methacrylate monomer and said second composition further contains an initiator and a crosslinking agent.

16. The article as defined in claim 7, wherein the volume ratio of the polyacrylic powder to the liquid acrylic monomer in said first composition about 3:1.

17. The article as defined in claim 7, wherein the volume ratio of the polyacrylic powder to the plasticized liquid acrylic monomer of said second composition is 3:1.

18. The article as defined in claim 11, wherein said copolymer comprises from about 70% combined methyl methacrylate and 30% combined ethyl methacrylate.

19. The article as defined in claim 7, in the form of a mandibular artificial denture having retro molar areas thereon formed from said second composition.

20. The article as defined in claim 7, wherein the teeth forming the anterior segment of said set are formed in said second composition, such that an adjustment of said anterior teeth is obtained when said assembly is heated and said second composition reaches its deforming temperature.

21. The article as defined in claim 7, wherein said first and second compositions are integrally formed such that no visual distinction therebetween is evident.

22. The article as defined in claim 21, wherein said frame portions are cured simultaneously so as to integrally form same.

23. The article as defined in claim 7, wherein said liquid plasticizer is selected from the group consisting of dibutyl phthalate, butyl benzyl phthalate, dimethyl phthalate, dicyclohexyl phthalate, diisodecyl phthalate, dioctyl phthalate, butyl phthalyl butyl glycolate, isodecyl diphenyl phosphate, alkyl benzyl phthalate, and mixtures thereof.

* * * * *